United States Patent
Baroni et al.

[11] Patent Number: 6,124,318
[45] Date of Patent: Sep. 26, 2000

[54] DIPHENYLALKYL-TETRAHYDROPYRIDINES, PROCESS FOR THEIR PREPARATION, AND PHARMACEUTICAL COMPOSITIONS CONTAINING THEM

[75] Inventors: Marco Baroni, Vanzago; Rosanna Cardamone, Como, both of Italy; Jacqueline Fournier, Plaisance du Touch, France; Umberto Guzzi, Milan, Italy

[73] Assignee: Sanofi-Synthelabo, Paris, France

[21] Appl. No.: 09/331,005

[22] PCT Filed: Dec. 11, 1997

[86] PCT No.: PCT/FR97/02289

§ 371 Date: Jul. 27, 1999

§ 102(e) Date: Jul. 27, 1999

[87] PCT Pub. No.: WO98/25904

PCT Pub. Date: Jun. 18, 1998

[30] Foreign Application Priority Data

Dec. 13, 1996 [FR] France ................ 9615336

[51] Int. Cl.⁷ .......... A61K 31/445; C07D 277/04; C07D 277/18; C07D 277/38
[52] U.S. Cl. .......... 514/317; 514/318; 546/192; 546/193
[58] Field of Search .......... 546/192, 193; 514/317, 318

[56] References Cited

U.S. PATENT DOCUMENTS

| 3,954,871 | 5/1976 | Buu-Hoi et al. | 260/570.6 |
| 5,109,005 | 4/1992 | Croci et al. | 514/277 |
| 5,229,389 | 7/1993 | Coude et al. | 514/260 |
| 5,266,573 | 11/1993 | Croci | 514/277 |
| 5,270,320 | 12/1993 | Coude et al. | 514/277 |
| 5,512,584 | 4/1996 | Steiner | 514/330 |
| 5,589,486 | 12/1996 | Harsanyi | 514/317 |
| 5,753,661 | 5/1998 | Moltzen | 514/254 |

FOREIGN PATENT DOCUMENTS

| 2158077 | 5/1972 | Germany. |
| WO 93/11107 | 6/1993 | WIPO. |

*Primary Examiner*—D. Margaret Seaman
*Attorney, Agent, or Firm*—Michael D. Alexander; Paul E. Dupont

[57] ABSTRACT

The invention relates to compounds of the formula

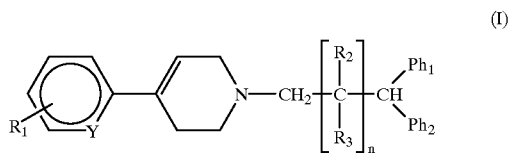

in which:
Y is —CH— or —N—;
$R_1$ is a halogen or a $CF_3$, $(C_1-C_4)$alkyl or $(C_1-C_4)$alkoxy group;
$R_2$ and $R_3$ are each hydrogen or a $(C_1-C_3)$alkyl;
n is 0 or 1; and
$Ph_1$ and $Ph_2$ are each independently an unsubstituted, mono-substituted or polysubstituted phenyl group;
to a process for their preparation and to the pharmaceutical compositions containing them.

These compounds have neurotrophic and neuroprotective activity.

34 Claims, No Drawings

DIPHENYLALKYL-TETRAHYDROPYRIDINES, PROCESS FOR THEIR PREPARATION, AND PHARMACEUTICAL COMPOSITIONS CONTAINING THEM

CROSS REFERENCE TO RELATED APPLICATIONS

This application is a filing under 35 U.S.C. § 371 corresponding to International Application Serial No. PCT/FR97/02289, filed Dec. 12, 1997, which claims priority of French Patent Application Serial No. FR 96 15336, filed Dec. 13, 1996.

The present invention relates to novel 4-substituted gem-diphenylalkyl-1,2,3,6-tetrahydropyridines with neurotrophic and neuroprotective activity, to a process for their preparation and to pharmaceutical compositions containing them.

EP-0 458 696 describes the use of a 1-(2-naphthylethyl)-4-(3-trifluoromethylphenyl)-1,2,3,6-tetrahydropyridine for the preparation of drugs intended for the treatment of cerebral and neuronal disorders.

It has now been found that certain gem-diphenylalkyl-1,2,3,6-tetrahydropyridines substituted by a phenyl or pyridyl group exert a neurotrophic action on the nervous system which is similar to the action of nerve growth factor (NGF), and can restore the function of damaged cells or cells exhibiting anomalies in their physiological functions.

According to one of its features, the present invention therefore relates to the gem-diphenylalkyl-1,2,3,6-tetrahydropyridines of formula (I):

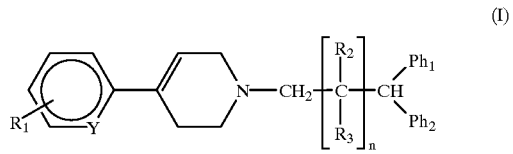

in which:

Y is —CH— or —N—;
$R_1$ is a halogen or a $CF_3$, $(C_1–C_4)$alkyl or $(C_1–C_4)$alkoxy group;
$R_2$ and $R_3$ are each hydrogen or a $(C_1–C_3)$alkyl;
n is 0 or 1; and
$Ph_1$ and $Ph_2$ are each independently an unsubstituted, monosubstituted or polysubstituted phenyl group;

and their salts and solvates and their quaternary ammonium salts.

Advantageous compounds according to the present invention are those of formula (I) in which Y is CH and $R_1$ is $CF_3$ and those of formula (I) in which Y is N and $R_1$ is Cl.

Among these compounds, those of formula (I) in which, in addition, $R_2$ and $R_3$ are both hydrogens and n is 0 or 1 are particularly advantageous.

Particularly advantageous compounds are represented by formula (I'):

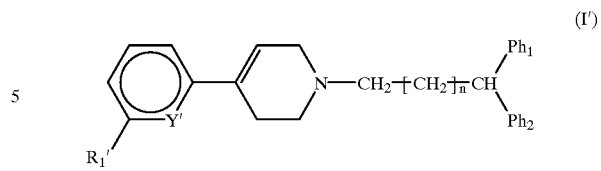

in which $R_1'$ is $CF_3$ and Y' is CH, or $R_1'$ is Cl and Y' is N, and n is zero or 1, $Ph_1$ and $Ph_2$ being as defined above.

In formulae (I) and (I'), $Ph_1$ and $Ph_2$ are preferably identical but they can also be different, implying the existence of a chiral carbon atom.

Advantageously $Ph_1$ and $Ph_2$ are each independently a phenyl group; a phenyl group monosubstituted in the 2-, 3- or 4-position by a fluorine or chlorine atom or by a methyl, ethyl, n-propyl, i-propyl, n-butyl, i-butyl, s-butyl, t-butyl, trifluoromethyl, cyano, methoxy, methylthio, methylsulfonyl, ethoxy, ethylthio, ethylsulfonyl, $(C_1–C_3)$alkoxycarbonyl or di$(C_1–C_3)$alkylaminocarbonyl group; a phenyl group disubstituted in the 2,4-, 3,4-, 3,5- or 2,6-positions by a fluorine or chlorine atom or by a methyl, ethyl, trifluoromethyl, cyano or methoxy group; or a phenyl group trisubstituted in the 3,4,5-, 2,4,5- or 2,4,6-positions by a chlorine or fluorine atom or by a methyl, ethyl, trifluoromethyl, cyano or methoxy group.

If $Ph_1$ and $Ph_2$ are different, one of the phenyl groups is preferably unsubstituted and the other is preferably monosubstituted in the 2-, 3- or 4-position as indicated above.

In the present description the term "$(C_1–C_3)$alkyl" denotes methyl, ethyl, n-propyl and i-propyl groups.

The term "alkoxy" denotes a hydroxyl group substituted by a $(C_1–C_4)$alkyl group.

The following compounds are particularly preferred:
1-(2,2-diphenylethyl)-4-(3-trifluoromethylphenyl)-1,2,3,6-tetrahydropyridine;
1-[2,2-(4,4'-dichlorodiphenyl)ethyl]-4-(3-trifluoromethylphenyl)-1,2,3,6-tetrahydropyridine;
1-[2,2-(3,3'-bistrifluoromethyldiphenyl)ethyl]-4-(3-trifluoromethylphenyl)- 1,2,3,6-tetrahydropyridine;
1-[2,2-(4,4'-dimethoxydiphenyl)ethyl]-4-(3-trifluoromethylphenyl)-1,2,3,6-tetrahydropyridine;
1-[2-(4-fluorophenyl)-2-phenylethyl]-4-(3-trifluoromethylphenyl)-1,2,3,6-tetrahydropyridine;
1-(3,3-diphenylpropyl)-4-(3-trifluoromethylphenyl)-1,2,3,6-tetrahydropyridine;
1-[2,2-(4,4'-dichlorodiphenyl)ethyl]-4-(6-chloropyrid-2-yl)-1,2,3,6-tetrahydropyridine;
and their salts, solvates or quaternary ammonium salts.

According to another of its features, the present invention relates to a process for preparing the compounds of formula (I), their salts or solvates and their quaternary amrnonium salts, characterized in that:

(a) an aryl-1,2,3,6-tetrahydropyridine of formula (II):

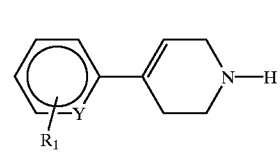

in which Y and $R_1$ are as defined above, is reacted with an acid of formula (III):

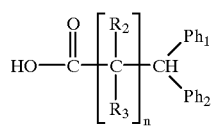
(III)

in which n, $R_2$, $R_3$, $Ph_1$ and $Ph_2$ are as defined above, or one of its functional derivatives;

(b) the intermediate carbonyl of formula (IV):

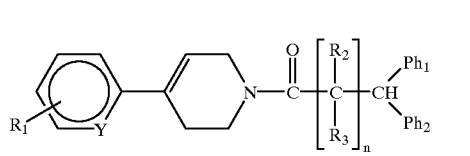
(IV)

is reduced; and (c) the resulting compound of formula (I) is isolated and optionally converted to one of its salts or solvates or one of its quaternary ammonium salts.

The reaction of step (a) can conveniently be carried out in an organic solvent at a temperature between −10° C. and the reflux temperature of the reaction mixture; the reaction is preferably carried out at low temperature.

The reaction solvent used is preferably a halogenated solvent such as methylene chloride, dichloroethane, 1,1,1-trichloroethane, chloroform or the like, or an alcohol such as methanol or ethanol, but it is also possible to use other organic solvents compatible with the reactants employed, for example dioxane, tetrahydrofuran or a hydrocarbon such as hexane.

The reaction can conveniently be carried out in the presence of a proton acceptor, for example an alkali metal carbonate or a tertiary amine. Appropriate functional derivatives of the acid of formula (III) which can be used are the free acid, which may be activated (for example with BOP), the anhydride, a mixed anhydride, an activated ester or an acid halide, preferably the chloride or bromide. Among the activated esters, the p-nitrophenyl ester is particularly preferred, but the methoxyphenyl, trityl, benzhydryl and similar esters are also convenient.

The reduction of step (b) can conveniently be carried out by means of appropriate reducing agents such as aluminum hydrides or a complex hydride of lithium and aluminum, in an inert organic solvent, at a temperature between 0° C. and the reflux temperature of the reaction mixture, according to the customary techniques.

"Inert organic solvent" is understood as meaning a solvent which does not interfere with the reaction. Examples of such solvents are ethers such as diethyl ether, tetrahydrofuran, dioxane or 1,2-dimethoxyethane.

The compound of formula (I) obtained is isolated by the conventional techniques and optionally converted to one of its acid addition salts; alternatively, if an acid group is present, the amphoteric character of the compound enables the salts to be separated either with acids or with bases.

If the salts of the compound of formula (I) are prepared for administration as drugs, the acids or bases employed must be pharmaceutically acceptable; if salts of the compound of formula (I) are prepared for another purpose, for example to improve the purification of the product or to better carry out analytical assays, any acid or base may then be used.

Examples of the salts with pharmaceutically acceptable acids are those with mineral acids, such as the hydrochloride, hydrobromide, borate, phosphate, sulfate, hydrogensulfate, hydrogenphosphate and dihydrogenphosphate, and those with organic acids, such as the citrate, benzoate, ascorbate, methylsulfate, naphthalene-2-sulfonate, picrate, fumarate, maleate, malonate, oxalate, succinate, acetate, tartrate, mesylate, tosylate, isethionate, α-ketoglutarate, α-glycerophosphate, glucose-1-phosphate, etc.

Examples of the salts with pharmaceutically acceptable bases are those with alkali metals or alkaline earth metals such as sodium, potassium, calcium and magnesium, and those with organic bases such as amines, basic amino acids (lysine, arginine, histidine), trometamol, N-methylglutamine, etc.

The starting amines of formula (II) in which Y is CH are known compounds or they can be prepared by methods analogous to those used to prepare the known compounds.

The starting amines of formula (II) in which Y is N can be prepared by reacting the appropriate 2-halogenopyridine of formula (p):

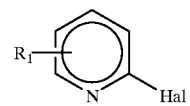
(p)

in which $R_1$ is as defined above and Hal is a halogen atom, with a 1,2,3,6-tetrahydropyridine of formula (q):

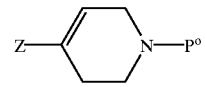
(q)

in which $P^o$ is a protecting group, for example the benzyl group, and Z is a substituent which allows the nucleophilic substitution of the pyridine halogen. Examples of such substituents are trialkylstannanes such as tributylstannane, or Grignard compounds.

The 1,2,3,6-tetrahydropyridine is then deprotected by cleavage of the protecting group under suitable conditions.

The acids of formula (III) in which n is 1 can be prepared by a Wittig reaction in which:

a) an appropriate benzophenone of formula (r):

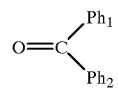
(r)

in which $Ph_1$ and $Ph_2$ are as defined above, is reacted with a compound of formula (s):

(s)

according to the Wittig reaction (as described for example in J. Med. Chem., 1996, 39(11), 2197–2206), b) the intermediate of formula (t):

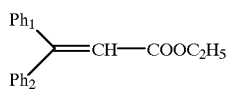

is then catalytically reduced in the presence of a catalyst such as Pd/C, and c) the intermediate of formula (u):

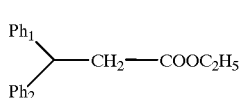

is optionally alkylated in the (x-position relative to the ester carbonyl, according to the known methods, if it is desired to prepare compounds of formula (I) in which $R_2$ and $R_3$ are other than hydrogen, and the ester of formula (v):

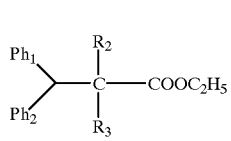

is hydrolyzed to give the acid of formula (III) in which n is 1.

The acids of formula (III) in which n is 0 can be prepared from the appropriate benzophenone of formula (r):

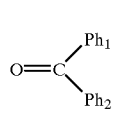

in which $Ph_1$ and $Ph_2$ are as defined above, by reaction with trimethylsulfoxonium iodide and oxidation of the intermediate aldehyde of formula (w):

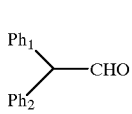

according to the method described in J. Am. Chem. Soc., 1990, 112(18), 6690–6695, to give the corresponding acid.

In another procedure the compounds of formula (I) in which n is 0 can also be prepared by reacting an aryl-1,2,3,6-tetrahydropyridine of formula (II):

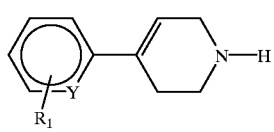

in which $R_1$ and Y are as defined above,
with an aldehyde of formula (w) above in the presence of a reducing agent such as sodium cyanoborohydride, according to the known techniques.

The activity of the compounds of formula (I) on the nervous system was demonstrated in in vitro and in vivo studies according to the methods described in EP-0 458 696 and, for evaluation of the neuronal survival, with the aid of an in vitro survival test carried out using neurons isolated from dissections of the septal region of rat embryos.

In this test the septal region of 17- to 18-day-old rat embryos is removed under a dissecting microscope under sterile conditions, is then dissociated in a trypsin/EDTA medium. The cellular suspension is placed in a culture flask in a DME/Ham's F12 (v:v) medium (Dulbecco Modified Eagle's medium/Ham's F12 nutrient mixture—R. G. Ham, Proc. Nat. Sci., 1965, 53, 288) containing 5% of calf serum and 5% of horse serum, and is kept at 37° C. for 90 minutes. This treatment makes it possible to remove the non-neuronal cells.

The neuroblasts are then inoculated at a rate of $17\times10^4$ cells/cm$^2$ into a non-serum culture medium consisting of DME/Ham's F12 medium containing selenium (30 nM) and transferrin (1.25 $\mu$M) in the wells of a titer plate. Each well has been treated with poly-L-lysine beforehand. The inoculated plates are placed in an incubator in the oven (37° C.; 5% $CO_2$).

The test compounds are dissolved in DMSO and diluted with the culture medium as required.

The neuroblasts are kept in plates containing the test compound or the corresponding solvent for 4 days without changing the medium.

After 4 days the medium is replaced with a tetrazolium salt dissolved in the culture medium (0.15 mg/ml). The cells are then placed in the oven at 37° C. for 4 hours. The mitochondrial succinate dehydrogenases of the living cells reduce the tetrazolium salt to formazan blue, whose optical density is measured at 540 nm after dissolution in DMSO. This density has a linear correlation with the number of living cells (Manthorpe et al., Dev. Brain Res., 1988, 25, 191–198).

The difference between the groups containing the test compounds and the controls was evaluated by statistical analysis using the two-tailed Dunnett t-test.

In said test the compounds of formula (I) were found to be as active as or more active than the compounds described in EP-0 458 696, the efficacy of certain compounds of formula (I) in respect of neuronal survival being twice that of compound A described in EP-0 458 696.

By virtue of this potent neuroprotective activity and their low toxicity compatible with use as drugs, the compounds of formula (I) and their pharmaceutically acceptable addition salts, their solvates and their quaternary ammonium salts can be used for the preparation of pharmaceutical compositions indicated in the treatment and/or prophylaxis of all diseases involving neuronal degeneration. More particularly, the compounds of the invention can be used, either by themselves or in co-administration or association with other active principles acting on CNS, for example acetylcholinesterase inhibitors, selective M1 cholinomimetics, NMDA antagonists and nootropics such as piracetam, especially in the following indications: memory disorders, vascular dementia, postencephalitic disorders, postapoplectic disorders, post-traumatic syndromes due to a cranial traumatism, disorders deriving from cerebral anoxia, Alzheimer's disease, senile dementia, subcortical dementia such as Huntington's chorea and Parkinson's disease, dementia caused by AIDS, neuropathies deriving from morbidity or damage to the sympathetic or sensory nerves, and brain diseases such as cerebral edema, and spinocerebellar degenerations and motor neuron degenerations, for example amyotrophic lateral sclerosis.

The compounds of the invention can conveniently be administered orally, parenterally, sublingually or transdermally. The amount of active principle to be administered in the treatment of cerebral and neuronal disorders by the method of the present invention depends on the nature and severity of the complaints to be treated and on the weight of the patients. Nevertheless the preferred unit doses will generally comprise from 0.25 to 700 mg, advantageously from 0.5 to 300 mg and preferably from 1 to 150 mg, for example between 2 and 50 mg, i.e. 2, 5, 10, 15, 20, 25, 30, 40 or 50 mg of product. These unit doses will normally be administered one or more times a day, for example 2, 3, 4 or 5 times a day and preferably one to three times a day, the overall dose in man varying between 0.5 and 1400 mg per day, advantageously between 1 and 900 mg per day, for example from 2 to 500 mg and more conveniently from 2 to 200 mg per day.

According to another of its features, the present invention relates to a pharmaceutical composition containing, as active principles, a compound of formula (I) above and a compound indicated in the symptomatic treatment of senile dementia of the Alzheimer type (DAT), or their pharmaceutically acceptable salts.

The expression "compound indicated in the symptomatic treatment of senile dementia of the Alzheimer type (DAT)" indicates a product which is capable of improving the symptomatological picture of patients suffering from DAT, without acting on the causes of the disease.

Examples of such compounds are acetylcholinesterase inhibitors, $M_1$ muscarinic agonists, nicotinic agonists, NMDA receptor antagonists and nootropics.

Preferred acetylcholinesterase inhibitors are donepezil and tacrine.

Examples of other acetylcholinesterase inhibitors which can be used are rivastigmine (SDZ-ENA-713), galanthamine, metrifonate, eptastigmine, velnacrine and physostigmine (Drugs, 1997, 53(5), 752–768; The Merck Index, 12th edition).

Other acetylcholinesterase inhibitors are 5,7-dihydro-3-[2-[1-(phenylmethyl)-4-piperidinyl]ethyl]-6H-pyrrolo[3,2-f]-1,2-benzisoxazol-6-one, also called icopezil (J. Med. Chem., 1995, 38, 2802–2808), MDL-73,745 or zifrosilone (Eur. J. Pharmacol., 1995, 276, 93–99) and TAK-147 (J. Med. Chem., 1994, 37, 2292–2299).

Examples of other acetylcholinesterase inhibitors are those described in patent applications JP 09-095483, WO 97/13754, WO 97/21681, WO 97/19929, ZA 96-04565, U.S. Pat. No. 5,455,245, WO 95-21822, EP 637 586, U.S. Pat. No. 5,401,749, EP 742 207, U.S. Pat. No. 5,547,960, WO 96/20176, WO 96/02524, EP 677 516, JP 07-188177, JP 07-133274, EP 649 846, EP 648 771, JP 07-048370, U.S. Pat. No. 5,391,553, WO 94/29272 and EP 627 400.

According to another of its features, the present invention relates to a pharmaceutical composition containing, as active principles, a compound of formula (I) and an $M_1$ receptor agonist or their pharmaceutically acceptable salts.

Examples of $M_1$ receptor agonists are milameline, besipiridine, talsaclidine, xanomeline, YM-796 and YM-954 (Eur. J. Pharmacol., 1990, 187, 479–486), 3-[N-(2-diethylamino-2-methylpropyl)-6-phenyl-5-propyl]pyridazinamine, also called SR-46559 (Biorg. Med. Chem. Let., 1992, 2, 833–838), AF-102, CI-979, L-689,660, LU 25-109, S-99 77-2, SB 202,026, thiopilocarpine and WAL 2014 (Pharmacol. Toxicol., 1996, 78, 59–68).

According to another of its features, the invention relates to a pharmaceutical composition containing, as active principles, a compound of formula (I) and a nicotinic agonist or their pharmaceutically acceptable salts.

Examples of advantageous nicotinic agonists are MKC-231 (Biorg. Med. Chem. Let., 1995, 5(14), 1495–1500), T-588 (Japan J. Pharmacol., 1993, 62, 81– 86) and ABT-418 (Br. J. Pharmacol., 1997, 120, 429–438).

According to another of its features, the invention relates to a pharmaceutical composition containing, as active principles, a compound of formula (I) and an NMDA receptor antagonist or their pharmaceutically acceptable salts.

An example of an advantageous NMDA receptor antagonist is memantine (Arzneim. Forsch., 1991, 41, 773–780).

According to another of its features, the invention relates to a pharmaceutical composition containing, as active principles, a compound of formula (I) and a nootropic agent or their pharmaceutically acceptable salts.

Examples of nootropic agents which can be used according to the invention are netiracetam and nebracetam (Merck Index, 12th edition).

The doses of the two associated active principles are generally chosen from the doses of each drug which would be administered in monotherapy.

According to a further feature, the present invention also relates to a method of treating senile dementia of the Alzheimer type, which consists in administering, to a patient suffering from this disease, an effective dose of a compound of formula (I) or one of its pharmaceutically acceptable salts and an effective dose of a compound indicated in the symptomatic treatment of DAT, or one of its pharmaceutically acceptable salts, said compounds being administered simultaneously, sequentially or spread over a period of time and it being possible for the effective doses of the active principles to be contained in separate unit forms of administration; alternatively, if the two active principles are administered simultaneously, they are advantageously contained in a single pharmaceutical form.

In the pharmaceutical compositions of the present invention for oral, sublingual, subcutaneous, intramuscular, intravenous, transdermal or rectal administration, the active principle can be administered to animals and humans in unit forms of administration, either as such, for example in lyophilized form, or mixed with conventional pharmaceutical carriers, for the treatment of the above-mentioned complaints. The appropriate unit forms of administration include oral forms such as tablets, which may be divisible, gelatin capsules, powders, granules and solutions or suspensions to be taken orally, sublingual and buccal forms of administration, subcutaneous, intramuscular or intravenous forms of administration, local forms of administration and rectal forms of administration.

When a solid composition in the form of tablets is prepared, the main active ingredient is mixed with a pharmaceutical vehicle such as gelatin, starch, lactose, magnesium stearate, talcum, gum arabic or the like. The tablets can be coated with sucrose or other appropriate substances or they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methylparaben and propylparaben as antiseptics, a flavoring and an appropriate color.

Water-dispersible powders or granules can contain the active ingredient mixed with dispersants or wetting agents, or with suspending agents such as polyvinylpyrrolidone, and with sweeteners or taste correctors.

Rectal administration is effected using suppositories, which are prepared with binders melting at the rectal temperature, for example cocoa butter or polyethylene glycols.

Parenteral administration is effected using aqueous suspensions, saline solutions or injectable sterile solutions containing pharmacologically compatible dispersants and/or wetting agents, for example propylene glycol or butylene glycol.

The active principle can also be formulated as microcapsules, optionally with one or more carriers or additives.

In the pharmaceutical compositions according to the present invention, the active principle can also be in the form of an inclusion complex in cyclodextrins, their ethers or their esters.

The Examples which follow illustrate the invention more clearly without however limiting it.

EXAMPLE 1

1-(2,2-Diphenylethyl)-4-(3-trifluoromethylphenyl)-1,2,3,6-tetrahydropyridine and its hydrochloride 1a/ 1-(α,α-Diphenylacetyl)-4-(3-trifluoromethylphenyl)-1,2,3,6-tetrahydropyridine 8 g of α,α-diphenylacetyl chloride in 50 ml of methylene chloride are added dropwise at a temperature of 0/+5° C. to a mixture of 8 g (0.035 mol) of 4-(3-trifluoromethylphenyl)-1,2,3,6-tetrahydropyridine, 50 ml of methylene chloride and 4.96 ml of triethylamine. The reaction mixture is stirred for one hour at room temperature, the solvent is evaporated off under reduced pressure and the residue is taken up with ethyl ether and washed with a 0.2 M aqueous hydrochloric acid solution, with water, with an aqueous sodium carbonate solution and again with water. It is dried over sodium sulfate and the solvent is evaporated off under reduced pressure to give 5 g of the title compound.

1b/ 1-(2,2-Diphenylethyl)-4-(3-trifluoromethylphenyl)-1,2,3,6-tetrahydropyridine and its hydrochloride A solution of 5 g (0.012 mol) of the product of the previous step in 50 ml of ethyl ether is added dropwise at 25° C. to a mixture of 0.7 g of lithium aluminum hydride in 10 ml of ethyl ether. The reaction mixture is stirred at room temperature for one hour and 5 ml of water are added dropwise. The two phases are separated, the organic phase is dried over sodium sulfate and the solvent is evaporated off under reduced pressure to give 1-(2,2-diphenylethyl)-4-(3-trifluoromethylphenyl)-1,2,3,6-tetrahydropyridine. The hydrochloride is prepared with a saturated solution of hydrochloric acid in ethyl ether. It is crystallized from 150 ml of ethyl acetate. M.p. (hydrochloride) 207–210° C.

EXAMPLE 2

1-[2,2-(4,4'-Dichlorodiphenyl)ethyl]-4-(3-trifluoromethylphenyl)-1,2,3,6-tetrahydropyridine and its oxalate 2a/ α, α(4,4'-Dichlorodiphenlyl)acetaldehyde 0.75 g (0.025 mol) of an 80% dispersion of sodium hydride in oil is added in portions to a mixture of 5.5 g (0.025 mol) of trimethylsulfoxonium iodide in 10 ml of anhydrous tetrahydrofuran. The reaction mixture is heated at 55° C. for 6 hours and 6 g (0.025 mol) of 4,4'-dichlorobenzophenone in 10 ml of anhydrous tetrahydrofuran are added. The mixture is stirred at 55° C. overnight, poured into water and extracted with ethyl ether, the organic phase is dried over sodium sulfate and the solvent is evaporated off under reduced pressure. The residue is dissolved in 32 ml of toluene, and 3 ml of $BF_3$-EtO are added. The mixture is stirred for 2 minutes and then left to stand for 3 minutes. It is washed twice with an aqueous sodium bicarbonate solution, the organic phase is dried over sodium sulfate and the solvent is evaporated off under reduced pressure to give an oil, which is purified by chromatography on a silica gel column using a 9/1 hexane/ethyl acetate mixture as the eluent to give the title compound.

2b/ 1-[2,2-(4,4'-Dichlorodiphenyl)ethyl]-4-(3-trifluoromethylphenyl)-1,2,3,6-tetrahydropyridine and its oxalate 1.3 g (0.0045 mol) of the product of the previous step, 1.2 g (0.0053 mol) of 4-(3-trifluoromethylphenyl)-1,2,3,6-tetrahydropyridine, 21 ml of methanol, 0.8 ml of glacial acetic acid and 0.5 g of anhydrous sodium acetate are mixed at a temperature of 0/+5° C. 0.76 g (0.0121 mol) of sodium cyanoborohydride is added to the mixture at the same temperature and the resulting mixture is stirred at low temperature for 1.5 hours and then at room temperature overnight. 5 ml of concentrated hydrochloric acid are added dropwise, the mixture is stirred for 10 minutes, the methanol is evaporated off and the residue is taken up with a mixture of ethyl acetate and dilute aqueous $NH_4OH$ solution. The two phases are separated, the organic phase is dried over sodium sulfate and the solvent is evaporated off under reduced pressure to give an oil, which is purified by chromatography on a silica gel column using a 9/1 hexane/ethyl acetate mixture as the eluent to give the title compound in the form of the base. The oxalate is prepared with oxalic acid in isopropanol. M.p. (oxalate) 187–189° C.

EXAMPLE 3

1-[2,2-(3,3'-Bistrifluoromethyldiphenyl)ethyl]-4-(3-trifluoromethylphenyl)-1,2,3,6-tetrahydropyridine and its oxalate 3a/ α,α-(3,3'-Bistrifluoromethyldiphenyl)acetaldehyde The title compound is obtained by the procedure described in Example 2a/ except that 3,3'-bistrifluoromethylbenzophenone is used.

3b/ 1-[2,2-(3,3'-Bistrifluoromethyldiphenyl)ethyl]-4-(3-trifluoromethylphenyl)-1,2,3,6-tetrahydropyridine and its oxalate The title compounds are obtained by the procedure described in Example 2b/ except that the product of the previous step is used instead of α,α-(4,4'-dichlorodiphenyl)acetaldehyde. M.p. (oxalate) 194–196° C.

EXAMPLE 4

1-[2,2-(4,4'-Dimethoxydiphenyl)ethyl]-4-(3-trifluoromethylphenyl)-1,2,3,6-tetrahydropyridine and its hydrochloride 4a/ α,α-(4,4'-Dimethoxydiphenyl)acetaldehyde The title compound is obtained by the procedure described in Example 2a/ except that 4,4'-dimethoxybenzophenone is used.

4b/ 1-[2,2-(4,4'-Dimethoxydiphenyl)ethyl]-4-(3-trifluoromethylphenyl)-1,2,3,6-tetrahydropyridine and its hydrochloride The title compounds are obtained by the procedure described in Example 2b/ except that the product of the previous step is used instead of α,α-(4,4'-dichlorodiphenyl)acetaldehyde. M.p. (hydrochloride) 214–216° C.

EXAMPLE 5

1-[2-(4-Fluorophenyl)-2-phenylethyl]-4-(3-trifluoromethylphenyl)-1,2,3,6-tetrahydropyridine and its hydrochloride 5a/ α-4-Fluorophenyl-α-phenylacetaldehyde The title compound is obtained by the procedure described in Example 2a/ except that 4-fluorobenzophenone is used.

5b/ 1-[2,2-(4-Fluorophenyl)-2-phenylethyl]-4-(3-trifluoromethylphenyl)-1,2,3,6-tetrahydropyridine and its hydrochloride The title compounds are obtained by the procedure described in Example 2b/ except that the product of the previous step is used instead of α,α-(4,4'-dichlorodiphenyl)acetaldehyde. M.p. (hydrochloride) 206–208° C.

EXAMPLE 6

1-(3,3-Diphenylpropyl)-4-(3-trifluoromethylphenyl)-1,2,3,6-tetrahydropyridine and its hydrochloride The title compounds are obtained by the procedure described in Example 1b/ except that commercial 3,3-diphenylpropionic acid (Aldrich, reference D21,165-6) is used instead of 2,2-diphenylacetic acid. M.p. (hydrochloride) 176–178° C.

EXAMPLE 7

1-[2,2-(4,4'-Dichlorodiphenyl)ethyl]-4-(6-chloropyrid-2-yl)-1,2,3,6-tetrahydropyridine and its hydrochloride The title compound is obtained by the procedure described in Example 2b/ except that 4-(6-chloropyrid-2-yl)-1,2,3,6-tetrahydropyridine is used instead of 4-(3-trifluoromethylphenyl)-1,2,3,6-tetrahydropyridine. M.p. (hydrochloride) 230–32° C.

EXAMPLE 8

1-[2,2-(4,4'-Difluorodiphenyl)ethyl]-4-(3-trifluoromethylphenyl)-1,2,3,6-tetrahydropyridine hydrochloride 1-[2,2-(4,4'-Difluorodiphenyl)ethyl]-4-(3-trifluoromethylphenyl)-1,2,3,6-tetrahydropyridine is obtained by the procedure described in Example 2 except that 4,4'-difluorobenzophenone is used instead of 4,4'-dichlorobenzophenone. The hydrochloride is prepared with a solution of hydrochloric acid in isopropanol to give the title compound. M.p. 173–175° C.

EXAMPLE 9

1-[2,2-(4,4'-Dichlorodiphenyl)ethyl]-4-(2-trifluoromethylphenyl)-1,2,3,6-tetrahydropyridine hydrochloride 9a/ 4-Hydroxy-4-(2-trifluoromethylphenyl)piperidine hydrochloride 3.25 g (0.135 mol) of Mg are mixed with a spatula tipfull of $I_2$, and a solution of 30.4 g (0.135 mol) of 2-bromo-1-trifluoromethylbenzene in 125 ml of THF is added dropwise. The mixture is stirred for one hour at room temperature and 10.1 g (0.041 mol) of benzylpiperidone are added dropwise. The mixture is stirred for 1 hour at room temperature and a saturated ammonium chloride solution is added. After extraction with ethyl ether, the organic phase is dried and the solvent is evaporated off under reduced pressure. The product is purified by chromatography on a silica gel column using a cyclohexane/ethyl acetate mixture as the eluent to give 6.8 g of 1-benzyl-4-hydroxy-4-(2-trifluoromethylphenyl)piperidine, which is hydrogenated with the aid of 0.7 g of 10% Pd/C in 75 ml of 95% ethanol which has been brought to acid pH by the addition of hydrochloric acid, the mnixture being heated at a temperature of 60° C. for 8 hours. The catalyst is filtered off to give 2.1 g of the title product. M.p. 247–251° C.

9b/ 4-(2-Trifluoromethylphenyl)-1,2,3,6-tetrahydropyridine hydrochloride 2.0 g (0.007 mol) of the product of the previous step are dissolved in 12 ml of glacial acetic acid. 3 ml of concentrated sulfuric acid are added dropwise and the mixture is heated at 100° C. for two hours. It is poured onto ice, a concentrated NaOH solution is added until the pH is basic, and the mixture is extracted with methylene chloride. The organic phase is dried and the solvent is evaporated off under reduced pressure. The product is taken up with 15 ml of isopropanol to give 4-(2-trifluoromethylphenyl)-1,2,3,6-tetrahydropyridine. The hydrochloride is prepared with a solution of hydrochloric acid in isopropanol to give 0.9 g of the title compound. M.p. 213–215° C.

9c/ 1-[2,2-(4,4'-Dichlorodiphenyl)ethyl]-4-(2-trifluoromethylphenyl)-1,2,3,6-tetrahydropyridine hydrochloride 0.5 g (0.0022 mol) of the product of the previous step in the form of the base, 9 ml of methanol, 0.33 ml of glacial acetic acid and 0.2 g of anhydrous sodium acetate are mixed at a temperature of 0/+5° C. 0.5 g (0.0019 mol) of α,α-(4,4'-dichlorodiphenyl)acetaldehyde, prepared according to Example 2a/, and then 0.33 g of sodium cyanoborohydride are added to the mixture at the same temperature and the resulting mixture is stirred at low temperature for 1.5 hours and then at room temperature overnight. 2.1 ml of concentrated hydrochloric acid are added dropwise, the mixture is stirred for 15 minutes, the methanol is evaporated off and the residue is taken up with a mixture of ethyl acetate and dilute aqueous $NH_4OH$ solution. The organic phase is dried, a saturated solution of hydrochloric acid in isopropanol is added and the solvent is evaporated off to give 0.48 g of the title compound, which is crystallized from ethyl acetate. M.p. 229–230° C.

What is claimed is:

1. A compound, or a salt, solvate or quaternary ammonium salt thereof, represented by formula (I):

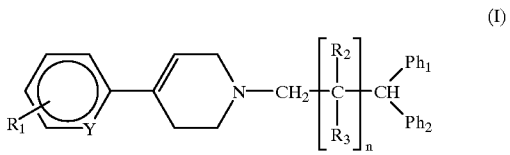

(I)

in which:

Y is —CH— or —N—;

$R_1$ is a halogen or a $CF_3$, $(C_1–C_4)$alkyl or $(C_1–C_4)$alkoxy group;

$R_2$ and $R_3$ are each hydrogen or $(C_1–C_3)$alkyl;

n is 0 or 1; and $Ph_1$ and $Ph_2$ are each independently an unsubstituted, monosubstituted or polysubstituted phenyl group.

2. A compound, or a salt, solvate or quaternary ammonium salt according to claim 1 in which Y is CH and $R_1$ is $CF_3$, or Y is N and $R_1$ is Cl.

3. A compound, or a salt, solvate or quaternary ammonium salt thereof, according to claim 1 in which wherein $R_2$ and $R_3$ are both hydrogens.

4. A compound, or a salt, solvate or quaternary ammonium salt thereof, according to claim 1 of formula (I'):

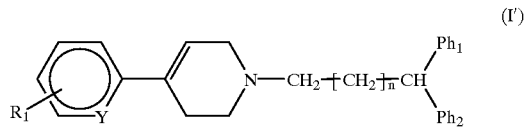

(I')

wherein $R_1$ is $CF_3$ and Y' is CH, or $R_1$ is Cl and Y' is N.

5. A compound, or a salts solvate or quaternary ammonium salt thereof, according to claim 1, wherein $Ph_1$ and $Ph_2$ are independently chosen from a phenyl group;

a phenyl group substituted in the 2-, 3- or 4-position by a fluorine or chlorine atom or by a methyl, ethyl, n-propyl, i-propyl, n-butyl, i-butyl, s-butyl, t-butyl, trifluoromethyl, cyano, methoxy, methylthio, methylsulfonyl, ethoxy, ethylthio, ethylsulfonyl, $(C_1-C_3)$alkoxycarbonyl or di$(C_1-C_3)$ alkylaminocarbonyl group;

a phenyl group wherein the 2,4-, 3,4-, 3,5- or 2,6-positions are independently substituted by a chlorine or fluorine atom or a methyl, ethyl, trifluoromethyl, cyano or methoxy group; and a phenyl group wherein the 3,4,5-, 2,4,5- or 2,4,6-positions are independently substituted by a chlorine or fluorine atom or a methyl, ethyl, trifluoromethyl, cyano or methoxy group.

6. A compound, or a salt, solvate or quaternary ammonium salt thereof, according to claim 5 in which $Ph_1$ and $Ph_2$ are identical.

7. A compound, or a salt, solvate or quaternary ammonium salt thereof, according to claim 1 selected from 1-(2,2-diphenylethyl)-4-(3-trifluoromethylphenyl)-1,2,3,6-tetrahydropyridine; 1-[2,2-(4,4'-dichlorodiphenyl)ethyl]-4-(3-trifluoromethylphenyl)-1,2,3,6-tetrahydropyridine; 1-[2,2-(3,3'-bistrifluoromethyldiphenyl)ethyl]-4-(3-trifluoromethylphenyl)-1,2,3,6-tetrahydropyridine; 1-[2,2-(4,4'-dimethoxydiphenyl)ethyl]-4-(3-trifluoromethylphenyl)-1,2,3,6-tetrahydropyridine; 1-[2-(4-fluorophenyl)-2-phenylethyl]-4-(3-trifluoromethylphenyl)-1,2,3,6-tetrahydropyridine; 1-(3,3-diphenylpropyl)-4-(3-trifluoromethylphenyl)-1,2,3,6-tetrahydropyridine; 1-[2,2-(4,4'-dichlorodiphenyl)ethyl]-4-(6-chloropyrid-2-yl)-1,2,3,6-tetrahydropyridine; and their salts, solvates or quaternary ammonium salts.

8. A pharmaceutical composition comprising a compound, or a pharmaceutically acceptable salt thereof, according to claim 1.

9. A pharmaceutical composition comprising a compound, or a pharmaceutically acceptable salt thereof, according to claim 1, and a compound, or a pharmaceutically acceptable salt thereof, indicated in the symptomatic treatment of senile dementia of the Alzheimer type (DAT).

10. A compound, or a salt, solvate or quaternary ammonium salt thereof, according to claim 4, wherein $Ph_1$ and $Ph_2$ are independently chosen from a phenyl group;

a phenyl group substituted in the 2-, 3- or 4-position by a fluorine or chlorine atom or by a methyl, ethyl, n-propyl, i-propyl, n-butyl, i-butyl, s-butyl, t-butyl, trifluoromethyl, cyano, methoxy, methylthio, methylsulfonyl, ethoxy, ethylthio, ethylsulfonyl, $(C_1-C_3)$alkoxycarbonyl or di$(C_1-C_3)$ alkylaminocarbonyl group;

a phenyl group wherein the 2,4-, 3,4-, 3,5- or 2,6-positions are independently substituted by a chlorine or fluorine atom or a methyl, ethyl, trifluoromethyl, cyano or methoxy group; and a phenyl group wherein the 3,4,5-, 2,4,5- or 2,4,6-positions are independently substituted by a chlorine or fluorine atom or a methyl, ethyl, trifluoromethyl, cyano or methoxy group.

11. A method of preparing a compound, or a salt, solvate or quaternary ammonium salt thereof, of formula (I) according to claim 1, comprising the steps of:

(a) reacting an aryl-1,2,3,6-tetrahydropyridine of formula (II)

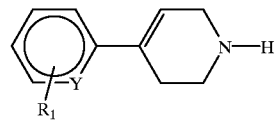

wherein Y and $R_1$ are as defined in claim 1,
with an acid, or a functional derivative thereof, of formula (III):

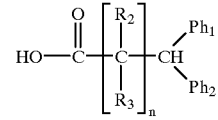

wherein n, $R_2$, $R_3$, $Ph_1$ and $Ph_2$ are as defined in claim 1, to obtain an intermediate carbonyl compound of formula (IV):

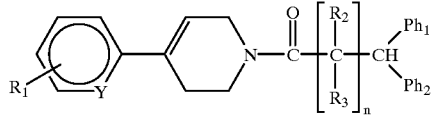

(b) reducing the compound of formula (IV); and
(c) isolating a compound of formula (I), which can optionally be converted into one of its salts or solvates or one of its quaternary ammonium salts.

12. A method for treating or preventing a disease associated with neuronal degeneration which comprises administering to a patient in need of such treatment a therapeutically effective amount of a compound of formula (I) according to claim 1, or a pharmaceutically acceptable salt thereof.

13. A method according to claim 12, wherein the therapeutically effective amount of a compound of formula (I) is between 0.5 and 1400 mg per day.

14. A method according to claim 13, wherein the therapeutically effective amount is between 2 and 200 mg per day.

15. A method according to claim 12, further comprising administering a therapeutically effective amount of a second compound, or a pharmaceutically acceptable salt thereof, indicated in the treatment of the disease associated with neuronal degeneration.

16. A method according to claim 15, wherein the second compound is chosen from the group consisting of acetylcholinesterase inhibitors, selective M1 cholinomimetics, NMDA antagonists and nootropics.

17. A method according to claim 12, wherein the disease associated with neuronal degeneration is selected from the group consisting of memory disorders, vascular dementia, postencephalitic disorders, postapoplectic disorders, post-traumatic syndromes due to cranial traumatism, disorders deriving from cerebral anoxia, Alzheimer's disease, senile dementia, subcortical dementia, AIDS-related dementia, neuropathies deriving from morbidity or damage to the sympathetic or sensory nerves, cerebral edema, spinocerebellar degenerations and motor neuron degenerations.

18. A method of treating senile dementia of the Alzheimer type (DAT), which comprises administering to a patient in need of such treatment, a therapeutically effective dose of a compound of formula (I) of claim 1 and a therapeutically effective dose of a compound indicated in the symptomatic treatment of DAT, or pharmaceutically acceptable salts thereof.

19. A method according to claim 18 wherein the compounds are administered simultaneously.

20. A method according to claim 19, wherein the compounds are contained in a single pharmaceutical form.

21. A pharmaceutical composition comprising a compound, or a pharmaceutically acceptable salt thereof, according to claim 2.

22. A pharmaceutical composition comprising a compound, or a pharmaceutically acceptable salt thereof, according to claim 3.

23. A pharmaceutical composition comprising a compound, or a pharmaceutically acceptable salt thereof, according to claim 4.

24. A pharmaceutical composition comprising a compound, or a pharmaceutically acceptable salt thereof, according to claim 5.

25. A pharmaceutical composition comprising a compound, or a pharmaceutically acceptable salt thereof, according to claim 6.

26. A pharmaceutical composition comprising a compound, or a pharmaceutically acceptable salt thereof, according to claim 7.

27. A pharmaceutical composition comprising a compound, or a pharmaceutically acceptable salt thereof, according to claim 10.

28. A method of treating or preventing a disease involving neuronal degeneration which comprises administering to a patient in need of such treatment a therapeutically effective amount of a compound, or a pharmaceutically acceptable salt thereof, according to claim 2.

29. A method of treating or preventing a disease involving neuronal degeneration which comprises administering to a patient in need of such treatment a therapeutically effective amount of a compound, or a pharmaceutically acceptable salt thereof, according to claim 3.

30. A method of treating or preventing a disease involving neuronal degeneration which comprises administering to a patient in need of such treatment a therapeutically effective amount of a compound, or a pharmaceutically acceptable salt thereof, according to claim 4.

31. A method of treating or preventing a disease involving neuronal degeneration which comprises administering to a patient in need of such treatment a therapeutically effective amount of a compound, or a pharmaceutically acceptable salt thereof, according to claim 5.

32. A method of treating or preventing a disease involving neuronal degeneration which comprises administering to a patient in need of such treatment a therapeutically effective amount of a compound, or a pharmaceutically acceptable salt thereof, according to claim 6.

33. A method of treating or preventing a disease involving neuronal degeneration which comprises administering to a patient in need of such treatment a therapeutically effective amount of a compound, or a pharmaceutically acceptable salt thereof, according to claim 7.

34. A method of treating or preventing a disease involving neuronal degeneration which comprises administering to a patient in need of such treatment a therapeutically effective amount of a compound, or a pharmaceutically acceptable salt thereof, according to claim 10.

\* \* \* \* \*

UNITED STATES PATENT AND TRADEMARK OFFICE
CERTIFICATE OF CORRECTION

PATENT NO. : 6,124,318
DATED : September 26, 2000
INVENTOR(S) : Marco Baroni; Rosanna Cardamone; Jacqueline Fournier & Umberto Guzzi It is certified that error appears in the above-identified patent and that said Letters Patent is hereby corrected as shown below:

Column 12, claim 2,
Line 49, insert -- thereof -- before according.

Claim 3,
Line 52, after "Claim 1" delete [in which].

Column 14, claim 12,
Line 37, after "disease" delete [associated with] and insert -- involving --.

Claim 15,
Line 50, after "disease" delete [associated with] and insert -- involving --.

Claim 17,
Line 57, after "disease" delete [associated with] and insert -- involving --.

Signed and Sealed this

Ninth Day of October, 2001

Attest:

NICHOLAS P. GODICI
Attesting Officer    Acting Director of the United States Patent and Trademark Office